United States Patent [19]

Van Wormer

[11] Patent Number: 5,259,837
[45] Date of Patent: Nov. 9, 1993

[54] ACOUSTICALLY ENHANCED CATHETER

[76] Inventor: Mark E. Van Wormer, 314 N. Third St., Clayton, N. Mex. 88415

[21] Appl. No.: 635,763

[22] Filed: Dec. 27, 1990

[51] Int. Cl.⁵ .......................................... A61M 29/00
[52] U.S. Cl. .................................... 604/96; 604/280; 128/658; 128/660.01
[58] Field of Search ............................... 128/656–658, 128/654, 660.1, 662.02, 662.03; 604/96, 101, 208, 264; 606/192, 194

[56] References Cited

U.S. PATENT DOCUMENTS

| | | | |
|---|---|---|---|
| 4,279,252 | 7/1981 | Martin | 128/349 R |
| 4,401,124 | 8/1983 | Guess et al. | 128/660 |
| 4,407,294 | 10/1983 | Vilkomerson | 128/660 |
| 4,431,006 | 2/1984 | Trimmer et al. | 128/660 |
| 4,512,762 | 4/1985 | Spears | 604/21 |
| 4,571,240 | 2/1986 | Samson et al. | 604/96 |
| 4,577,637 | 3/1986 | Mueller et al. | 128/658 |
| 4,582,061 | 4/1986 | Fry | 128/329 R |
| 4,637,401 | 1/1987 | Johnston | 128/663 |
| 4,674,336 | 6/1987 | Johnston | 73/861.25 |
| 4,697,595 | 10/1987 | Breyer | 128/660 |
| 4,771,777 | 9/1988 | Horzewski et al. | 604/101 X |
| 4,793,350 | 12/1988 | Mar et al. | 604/96 X |
| 4,793,359 | 12/1988 | Sharrow | 128/658 |
| 4,821,722 | 4/1989 | Miller et al. | 604/96 X |
| 4,838,879 | 6/1989 | Tanabe et al. | 604/280 |
| 4,869,259 | 9/1989 | Elkins | 128/660 |
| 4,913,142 | 4/1990 | Kittrell et al. | 606/7 |
| 4,917,666 | 4/1990 | Solar et al. | 604/95 |
| 4,946,466 | 8/1990 | Pinchuk et al. | 606/194 |
| 5,000,185 | 3/1991 | Yock | 128/662.03 |
| 5,054,492 | 10/1991 | Scribner et al. | 128/662.06 |

OTHER PUBLICATIONS

Abstract: "Positioning of Umbilical Arterial Chatheters with Ultrasound" by A. K. Garg et al., *Archives of Disease in Childhood*, pp. 1017–1018, Dec. 1983.

"Optimized Ultrasound Imaging Catheters for Use in the Vascular System" by R. J. Crowley et al., Abstract, *International Journal of Cardiac Imaging*, pp. 145–151, 1989.

Abstract: "Diagnostic Accuracy of Color Oppler Flow Imaging and Duplex US in Peripheral Arterial Disease", by M. I. Karmel et al.

"Transluminal Treatment of Arteriosclerotic Obstruction" by C. T. Dotter et al., *Radiology*, pp. 904–920, Sep. 1989.

"A Brief History of Vascular Intervention" by Robert J. Rosen.

"Long-Term Results of Superficial Femoral Artery Angioplasty" by Robert C. Hewes et al., AJR, 146, pp. 1025–1029, May 1986.

"Percutaneous Transluminal Dilation of the Iliac Artery: Long-Term Results" by G. J. van Andel et al., Radiology, 1095, vol. 156; pp. 321–323.

"Pre-Procesure Assessment and Choice of Modality, Angioplasty, Atherectomy, Laser—A Transatlantic View" by L. Machan.

"Balloon-Expandable Intravascular Stent" by Julio C. Palmaz, *AJR*, 150, pp. 1263–1269, Jun. 1988.

"Peripheral, Abdominal, and Interventional Applications of DSA" by Barry T. Katzen, *Radiologic Clinics of North America*, vol. 23, No. 2, Jun. 1984.

"Peroperative Monitoring of Distal Transluminal Dilation" by M. D. McShane et al., *Journal of Clinical Ultrasound*, vol. 16, pp. 659–662, Nov./Dec. 1988.

"Clinical Applications of a Transcutaneous Ultrasonic Flow Detector" by Robert F. Rushmer et al., *JAMA*, vol. 199, No. 5; pp. 104–106, Jan. 30, 1967.

(List continued on next page.)

*Primary Examiner*—C. Fred Rosenbaum
*Assistant Examiner*—Corrine Maglione
*Attorney, Agent, or Firm*—Donovan F. Duggan; Rod D. Baker; Deborah A. Peacock

[57] ABSTRACT

A percutaneous transluminal angioplasty or atherectomy catheter is acoustically enhanced by placing at least two ultrasonographically detectable markers, one at the proximal and one at the distal limits of the catheter balloon. The location of the catheter in the artery is thereby correctly positioned by ultrasonographic imaging.

22 Claims, 2 Drawing Sheets

OTHER PUBLICATIONS

"Ultrasonic Duplex Echo-Doppler Scanner" by Frank E. Barber et al., *IEEE Transactions of Biomedical Engineering*, vol. BME-21, No. 2, Mar. 1974.

"Recent Advances in Imaging and Evaluation of Blood Flow Using Ultrasound" by Alfred V. Persson et al., *Medical Clinics of North America*, vol. 70, No. 6, Nov. 1986.

"Transluminal Angioplasty of the Iliac Arteries" (Supplement), by Barry T. Katzen et al., *Seminars in Interventional Radiology*, vol. 2, No. 2, Jun. 1985.

"Postoperative Surveillance of Infrainguinal Bypass" by Dennis F. Bandyk, *Noninvasive Diagnosis of Vascular Diseases*, Surgical Clinics of North America, vol. 70, No. 1, Feb. 1990.

Kohler et al.; "Can Duplex Scanning Replace Arteriography For Lower Extremity Arterial Disease?", May 1990; Annals of Vascular Surgery; pp. 280-287; Abstract.

Cossman et al.; "Comparison of Contrast Arteriography to Arterial Mapping with Color-Flow Duplex Imaging in the Lower Extremities"; Nov. 1989; Journal of Vascular Surgery; pp. 522-528; Abstract.

Ellison et al.; "Accuracy of Color Flow Arterial Imaging of the Legs and its Application in Planning Intervention", Jun. 16, 1989; Scientific Session II; p. 137.

Phillips et al., "Detection of Peripheral Vascular Disease Using the Duplex Scanner III"; Dec. 1979; Ultrasound in Med. & Biol., vol. 6, pp. 205-218.

Boice et al.; "Carcinogenesis—A Synopsis of Human Experience with External Exposure in Medicine"; Oct. 1988; Health Physics; vol. 55, No. 4; pp. 621-630.

Laerum et al.; "Double Blind Evaluation of the Effects of Various Contrast Media on Extremity Veins in the Dog"; 1987; Acta Radiologica, 28; pp. 107-113.

Laerum; "Cytotoxic Effects of Six Angiographic Contrast Media on Human Endothelium in Culture"; May 1986; Acta Radiologica 28, (1987); pp. 99-105.

Hessel et al.; "Complications of Angiography"; Feb. 1981; Diagnostic Radiology; pp. 273-281.

Gomes et al.; "Acute Renal Dysfunction in High-Risk Patients After Angiography: Comparison of Ionic and Nonionic Contrast Media"; Jan. 1989; Radiology, vol. 170, No. 1, pp. 65-68.

Shehadi et al., "Adverse Reactions to Contrast Media", Nov. 1980; Diagnostic Radiology; pp. 299-302.

Morin et al.; "Factors That Determine the Long-Term Results of Percutaneous Transluminal Dilation for Peripheral Arterial Occlusive Disease"; Jul. 1986; Journal of Cascular Surgery; vol. 4, No. 1, pp. 68-72.

Ansell; "Adverse Reactions to Contrast Agents"; 1970; Investigative Radiology, vol. 5, No. 6; pp. 373-384.

Chapters 2-8, *Noninvasive Diagnosis of Peripheral Vascular Diease*, edited by W. Robert Felix, Jr., Raven Press, New York, (1987), pp. 31-170.

*5-Year Results of a Prospective Study of Percutaneous Transluminal Angioplasty*, presented at 107th Annual Meeting of the American Surgical Association, (1987), by K. W. Johnston, M.D., et al., pp. 403-413.

Chapter 1, *Noninvasive Diagnosis of Peripheral Vacular Disease* edited by W. Robert Felix, Jr., Raven Press, New York, (1987), pp. 5-29.

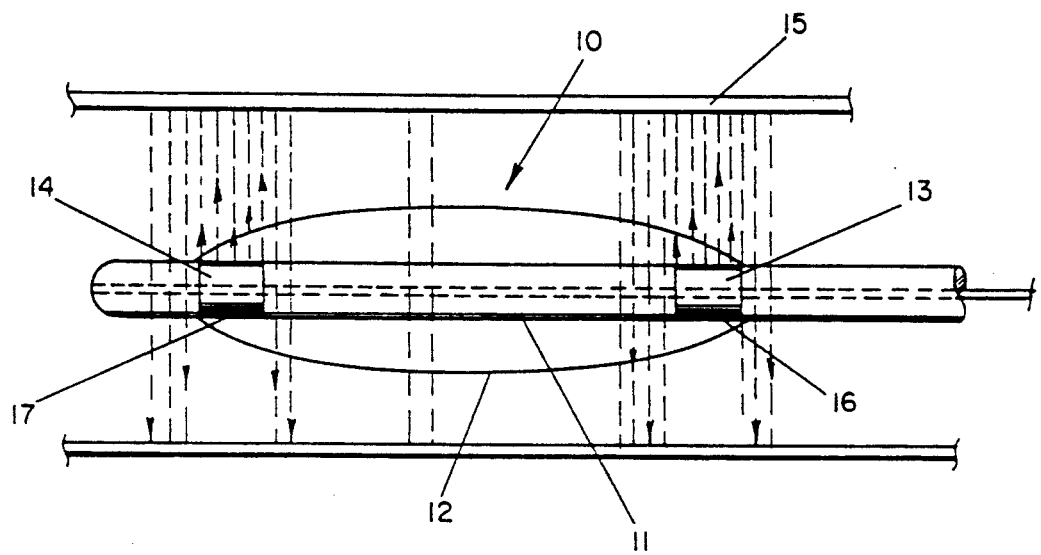
FIG—1
PRIOR ART
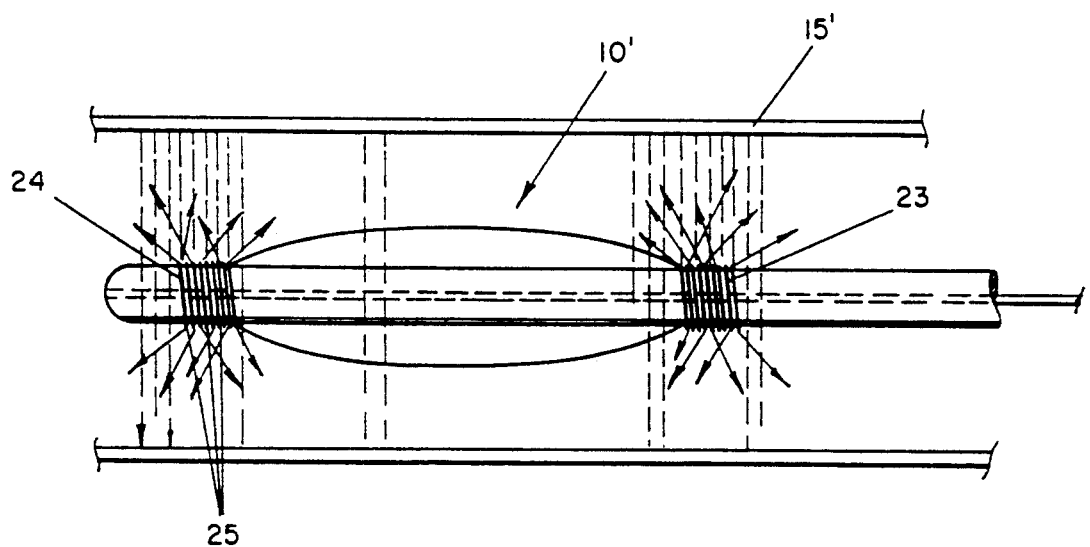
FIG—2

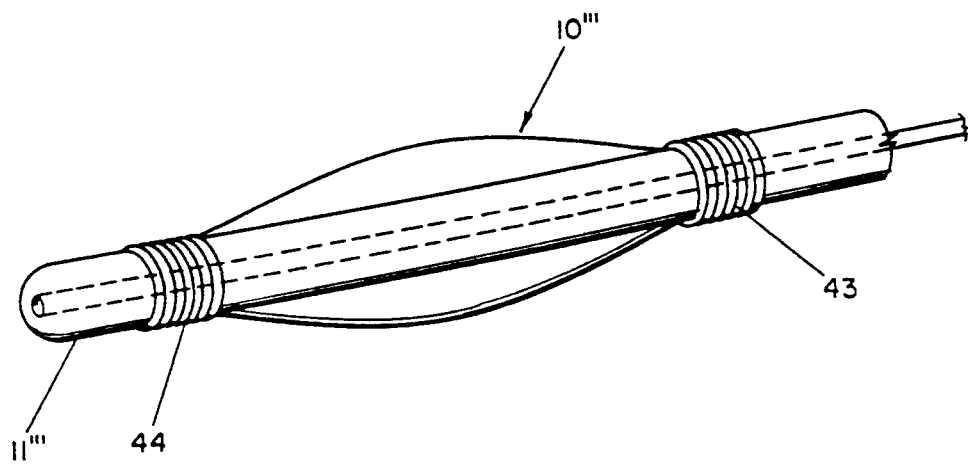
FIG—4
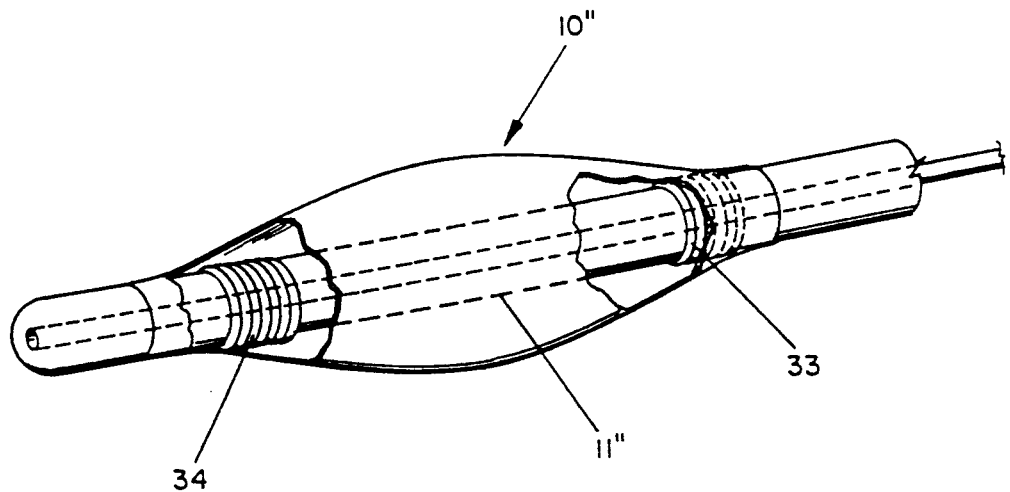
FIG—3

ACOUSTICALLY ENHANCED CATHETER

BACKGROUND OF THE INVENTION

1. Field of the Invention (Technical Field)

This invention relates to apparatuses for ultrasonic imaging of angioplasty or atherectomy catheters; and methods for their use.

2. Background Art

Standard percutaneous transluminal angioplasty, atherectomy, dilatation, and stenting techniques of the peripheral vascular system have traditionally required the use of iodinated contrast media and radiographic guidance for the proper positioning of the dilatation balloon across an arterial stenosis. There is a known incidence of allergy to iodinated contrast dye as well as unpredictable reactions to contrast dye, including various degrees of anaphylaxis and renal failure. The ionizing radiation utilized during the procedure is also a hazard to the patient and the medical staff.

Ultrasonographic imaging, on the other hand, presents no known irradiation hazard and requires no use of radiopaque contrast medium, yet provides excellent visualization of the arterial lumen and walls.

The correct placement of the angioplasty balloon during an angioplasty or atherectomy procedure is not only facilitated by the use of radiographic contrast medium to determine the location of the arterial stenosis, but also by radiographic markers, usually small bands of radiopaque material (metal), which mark the proximal and distal limits of the balloon.

The present invention allows for the correct placement of an angioplasty balloon catheter across an arterial stenosis utilizing ultrasonographic imaging alone, for example, B-mode imaging, thereby obviating contrast reactions and ionizing radiation exposure.

The concept of marking catheters with metallic elements is not new. Devices such as that disclosed in U.S. Pat. No. 4,279,252, to Martin, entitled *X-Ray Scaling Catheter*, utilize metallic foil rings embedded in the walls of an angiography catheter at a set distance apart in order to calculate distances within the heart and correct for errors due to x-ray magnification. These markers are radiopaque and designed for use with radiographically guided cardiac angiography procedures.

The concept of acoustically modifying catheters for enhanced visualization with ultrasound imaging is not per se novel. U.S. Pat. No. 4,401,124, to Guess, et al., entitled *Reflection Enhancement of a Biopsy Needle*, disclose a diffraction grating comprising parallel grooves etched into the tip of a biopsy needle for enhancing the reflection coefficient when used in conjunction with pulse-echo ultrasound imaging. Similarly, Elkins in U.S. Pat. No. 4,869,259 entitled *Echogenically Enhanced Surgical Instrument and Method for Production Thereof* discloses an acoustically enhanced surgical needle having a roughened surface with pits and erosions of the order of 50 microns in depth. The resultant roughness increases the density of reflected ultrasound beams to the piezoelectric sensor, resulting in enhanced echogenicity of the treated portion of the needle.

U.S. Pat. No. 4,431,006, to Trimmer, et al., entitled *Passive Ultrasound Needle Probe Locator*, teaches a sonically conductive needle which conveys ultrasonic energy to an external transducer. Divisional U.S. Pat. Nos. 4,637,401 and 4,674,336, to Johnston, entitled *Volumetric Flow Rate Determination in Conduits Not Directly Accessible*, both teach ultrasonic energy reflection in combination with a Doppler circuit for measuring blood velocity.

U.S. Pat. No. 4,582,061, to Fry, entitled *Needle with Ultrasonically Reflective Displacement Scale*, teaches a body puncturing device comprising a plurality of cavities or grooves for trapping gas, thereby improving acoustic reflection. U.S. Pat. No. 4,697,595, to Breyer, et al., entitled *Ultrasonically Marked Cardiac Catheters*, discloses a plurality of piezoelectric transducers embedded in a catheter to establish catheter location. U.S. Pat. No. 4,571,240, to Samson, et al., entitled *Catheter Having Encapsulated Tip Marker*, discloses a catheter comprising a broad metallic band at one end thereof for fluoroscopic use. U.S. Pat. No. 4,407,294, to Vilkomersas, entitled *Ultrasound Tissue Probe Localization System*, teaches an ultrasound imaging system comprising at least three transducers. U.S. Pat. No. 4,577,637, to Mueller, Jr., entitled *Flexible Metal Radiopaque Indicator and Plugs for Catheters*, discloses a radiopaque coiled metal spring which provides a catheter plug and indicator. U.S. Pat. No. 4,512,762, to Spears, entitled *Method of Treatment of Atherosclerosis and a Balloon Catheter for Same*, discloses a light-emitting balloon catheter for treatment of atheromatous plaque.

The current invention utilizes the placement of a fine wire monolayer, for example, 5 mm long, proximal and distal, at the limits, or within the angioplasty balloon itself, in order to be detected acoustically by ultrasonographic imaging. The proper detection of the proximal and distal limits of the angioplasty balloon by ultrasonographic imaging results in the ability to correctly position the balloon across an arterial stenosis without the use of radiographic contrast medium or ionizing radiation. Hence, angioplasty can be accomplished by non-radiographic ultrasonic guidance obviating the risks inherent to the traditional use of contrast agents and ionizing radiation.

SUMMARY OF THE INVENTION (Disclosure of the Invention)

The present invention relates to an acoustically enhanced catheter and methods of using the catheter. The catheter is elongated and has a proximal end and a distal end. Acoustic scattering markers are mounted on the catheter.

The acoustic scattering markers are preferably mounted proximally and distally on the catheter. If the catheter is a balloon catheter, the acoustic scattering markers may be mounted proximally and distally on the balloon, either internally of the balloon, or externally of the balloon.

The acoustic scattering markers preferably comprise coils, such as discrete annular coils or helical coils. The coils may be encapsulated by ultrasonically transparent material. Preferably the coils are in a monolayer. The acoustic scattering markers are preferably made from a metal, such as copper, gold, silver, platinum, stainless steel, or alloys thereof. The acoustic scattering markers preferably have a length in the range of approximately 3 to 7 millimeters, and most preferably approximately 5 millimeters.

An ultrasonic transducer is used to ultrasonically scan the catheter. Useful transducers include piezoelectric transducers and magnetostrictive transducers. The method of the invention for in vivo positioning of the catheter comprises the steps of (a) providing the catheter with at least one acoustic scattering device; (b) introducing the catheter into a vascular system; and (c) subjecting the catheter with ultrasonic energy and thereby guiding the catheter into the desired position in the vascular system.

It is an object of the present invention to provide an angioplasty or atherectomy catheter with acoustically enhanced balloon markers.

It is another object of the present invention to provide an echogenically enhanced angioplasty or atherectomy catheter which can be guided ultrasonographically.

A primary advantage of the present invention is that contrast dyes and radiation, which can be harmful to a patient, are not used.

Another advantage of the present invention is its ease of fabrication and emplacement.

Yet another advantage of the present invention is its ready adaptation to retrofitting existing balloon catheters.

Other objects, advantages, and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating a preferred embodiment of the invention and are not to be construed as limiting the invention.

FIG. 1 is a schematic side view of ultrasonic scanning of a prior art balloon catheter;

FIG. 2 is a schematic side view of ultrasonic scanning of a balloon catheter of the present invention;

FIG. 3 is a perspective view of the preferred embodiment of the present invention; and FIG. 4 is a perspective view of an alternative embodiment of the present invention.

DESCRIPTION OF THE PREFERRED EMBODIMENTS (Best Modes for Carrying out the Invention)

With specific reference to FIG. 1, ultrasonic scanning of a prior art balloon catheter is schematically illustrated therein. Balloon catheter 10 having a central lumen tube 11 and balloon lumen 12, is inserted into a blood vessel to be treated. As is well known in the art, balloon catheter 10, after inflation with pressurized gas, is normally and desirably directly in contact with, for example, an arterial stenosis to be lysed. Accurate placement of balloon catheter 10 is therefore critical for effective treatment.

Prior art placement techniques typically utilize broad metallic bands 13,14, more suitable for radiographic imaging. Theoretically, such broad metallic bands, or markers 13,14, when scanned (see dashed lines and arrows indicating direction of scanning) with ultrasonic energy from a transducer, schematically represented by 15, provide marking or boundary information (see arrows directed away from metallic bands 13,14) as to the proximal and distal location of balloon catheter 10. However, as depicted in FIG. 1, metallic bands 13,14, totally reflect such scanning ultrasonic energy. Acoustic shadows 16,17, are thereby created, obscuring acoustic information below acoustic markers 13,14.

FIGS. 2-3 illustrate the preferred balloon catheter of the present invention, showing acoustic markers. FIG. 4 illustrates an alternative embodiment of the present invention, showing a different positioning of the balloon relative to the acoustic markers.

FIG. 2 schematically illustrates acoustic effects created by use of the acoustic markers of the present invention and is applicable to the preferred and alternative embodiments. As shown therein, acoustic markers 23,24, positioned proximally and distally of balloon catheter 10', comprise a plurality of coils 25. Alternatively, an acoustic marker 23,24 could be positioned centrally of balloon catheter 10'. Coils 25, for example, may comprise separate and discrete annuli, or annular coils. Coils 25 may also comprise a plurality of the connected coils of a helix, or a helical coil. In either case, impinging ultrasonic energy from a transducer, schematically represented by 15', is effectively scattered when reflected (see arrows directed away from coils 25), resulting in a fuzzy, glowing image, easily traceable on a display monitor. In both embodiments, preferably only a single coil layer is employed thereby assuring adequate scattering of ultrasonic energy. Accordingly, proximal and distal ends of balloon catheter 10' are well marked; no acoustic shadows are present.

Ultrasonic transducer 15' preferably comprises a piezoelectric transducer. Alternatively, a magnetostrictive transducer could be utilized.

Coils 25 are preferably made of metal which can be detected using ultrasonic transducers, however, other materials detectable by ultrasound may be utilized in accordance with the invention. The individual coils 25 may, for example, comprise copper wire, preferably 30-gauge; alternatively, other metals such as gold, silver, platinum, stainless steel, alloys thereof, and the like, may be used. Aggregate length of the coils 25, whether discrete annular coils or a helix, preferably comprises a length in the range of 3 to 7 millimeters; 5 millimeters comprises an effective average length.

FIG. 3 schematically illustrates the preferred embodiment of the invention. Acoustical coil markers 33,34 are positioned within balloon catheter 10''. The envelope of balloon catheter 10'' prevents loss of the markers in the event of inadvertent detachment from the catheter, providing better safety for the patient. If acoustical coil markers each comprise a plurality of discrete annular coils, such coils may be secured together by ultrasonically transparent plastic. Such plastic may serve to bond, fuse, weld, or encapsulate the individual coils into a coherent mass. The ultrasonically transparent plastic may further secure the coils to central lumen tube 11''. If acoustic markers 33,34 comprise helices, they need only be secured, as aforementioned, to central lumen tube 11''.

FIG. 4 depicts an alternative embodiment of the invention. Proximal and distal acoustic markers 43,44 are positioned externally of balloon catheter 10'''. In this embodiment, whether discrete coils or helices are employed, encapsulation of markers 43,44 with a thin layer of ultrasonically transparent material (not shown) may be utilized in order to secure markers 43,44 to lumen tube 11'' and to prevent dislodgement of the markers into the arterial system, thereby providing safety to the patient. This transparent material, preferably a monolayer, should be thin enough so that the acoustic nature of the markers is not interfered with. Useful transparent materials include TEFLON ® or other heat shrink plastic materials.

In practice, acoustic markers 23,24 are initially positioned centrally or proximally and distally on a balloon catheter 10', and secured thereto. If positioned proximally and distally, markers 23,24 may additionally be positioned either externally or internally of balloon catheter 10'. If positioned externally of balloon catheter 10', additional securing means comprising a monolayer of acoustically transparent plastic and utilized.

As can be appreciated by those skilled in the art, the catheter need only comprise one or two acoustic markers or may comprise more than one acoustic markers. Placement of the acoustic markers depends on the desired application; for instance, acoustic markers may be positioned proximally, distally, centrally, or in combination thereof.

The preferred method of the invention for in vivo positioning of the catheter comprises the steps of providing the catheter with at least one acoustic scattering marker, introducing the catheter into a vascular system, and subjecting the catheter with ultrasonic energy and thereby guiding the catheter into the desired position in the vascular system. Introduction of the modified balloon catheter into the vascular system is accomplished by well-known techniques, for example, by insertion into the femoral artery. Transport of catheter 10' to the desired vascular area is accomplished simultaneously while irradiating and scanning catheter 10' with ultrasonic energy. Balloon catheter 10' is thus continually monitored and guided en route; ultrasonic scanning of acoustic markers 23,24 thus aids greatly in ultimate positioning of catheter 10'.

As can be appreciated by those skilled in the art, the acoustic markers of the present invention can be used in any type of catheter placement where ultrasonographic imaging is applied, particularly B-mode ultrasonographic imaging.

EXAMPLES

(Industrial Applicability)

The invention is further illustrated by the following non-limiting examples.

Imaging was performed utilizing a 5 megahertz phased linear array realtime colorflow doppler imaging system with 18 degree standoff wedge manufactured by Quantum Medical Systems, Issaquah, Wash. A tissue flow phantom was created by constructing an 8 inch × 6 inch × 7 inch PLEXIGLAS (trademark) box with 8 separate holes in each end for passage of surgical tubing with lumens measuring 5, 8, 10, 12, and 15 mm positioned at different angles to simulate arterial anatomy. Short segments of surgical tubing were modified into arterial stenoses by wrapping monofilament nylon line strategically around the tubing to create hemodynamically significant stenoses resembling those found in peripheral vascular arterial occlusive disease. The surgical tubing was suspended in an acoustic medium consisting of KNOX (trademark) gelatin and talcum powder. In order to create flow in these suspended vessels, a peripheral pumping device consisting of a Model 1-42A, 60 Hz, 1.1 amp., 115 volt continuous flow pump 31 with a 5 gallon reservoir containing 2 gallons of water and 1 cup of cornstarch was utilized. A closed circuit system was devised using a 4' segment of tubing running from the pump to the flow phantom in order to create a long segment of prearterial laminar flow. The suspension of cornstarch acted as the acoustic medium simulating the scattering qualities of red blood cells. Initial testing for flow characteristics utilizing the phantom was considered successful in simulating normal human arterial flow, although it was not pulsed. Acoustically, the arterial segments of surgical tubing appeared comparable to living human vessel with visible vascular walls and measurable functionable lumens resultant from the flowing acoustic medium. Laminar flow in the nonstenotic areas was present. At sites of artificial stenoses, the poststenotic flow characteristics were consistent with those found in human stenoses; marked turbulence and spectral broadening as well as elevated flow velocities in the 180 to 200 cm per second range typical of the hemodynamically significant stenoses. Prestenotic flow generally measured between 75 and 80 cm per second also similar to flow in large human arteries. With the introduction into the arterial system of an 11 french introducer, while simultaneously imaging flow, the modified balloon angioplasty catheter was positioned. From previous experiments, it had been demonstrated that there were difficulties in determining the proximal and distal balloon margins. The catheter itself was also very difficult to visualize under color-flow conditions intraluminally. With the modified catheter, however, there was no problem in visualizing the catheter location within the vascular lumen. The copper coils acted as a "soft" acoustic reflector, literally scattering ultrasound rather than reflecting it perpendicularly back to the scanhead. This was evidenced by the lack of acoustic shadowing emanating from the coils; instead, the presence of a hazy, glowing, appearance of the reflectors. The curvature of the multiple closely placed copper wires most likely resulted in an artifact creating only focal displacement of colorflow data but not acoustic shadowing which might obscure evaluation of the posterior anatomy of the arterial segment being approached. B-Mode imaging also provided excellent visualization of the catheter markers as well.

Although the invention has been described with reference to these preferred embodiments, other embodiments can achieve the same results. Variations and modifications of the present invention will be obvious to those skilled in the art and it is intended to cover in the appended claims all such modifications and equivalents.

What is claimed is:

1. An acoustically enhanced catheter for use in a body lumen comprising:

an elongated catheter having a proximal end and a distal end;

coiled means for scattering ultrasonic energy, said scattering means encapsulated by ultrasonically transparent material and mounted on said catheter; and ultrasonic transducer means, disposed externally of the body lumen, for ultrasonically scanning said catheter.

2. The invention of claim 1 wherein said catheter comprises a balloon catheter having a balloon.

3. The invention of claim 2 wherein said coiled means for scattering ultrasonic energy are mounted proximally and distally on said balloon.

4. The invention of claim 3 wherein said coiled means for scattering ultrasonic energy are mounted proximally and distally internally of said balloon.

5. The invention of claim 3 wherein said coiled means for scattering ultrasonic energy are mounted proximally and distally externally of said balloon.

6. The invention of claim 1 wherein said coiled means for scattering ultrasonic energy are mounted proximally and distally on said catheter.

7. The invention of claim 1 wherein said ultrasonic energy scattering means comprises discrete annular coils, wherein the distance between adjacent discrete annular coils is less than the length of the annulus diameter.

8. The invention of claim 1 wherein said ultrasonic energy scattering means comprises a helical coil.

9. The invention of claim 1 wherein said ultrasonic energy scattering means comprises a coil monolayer.

10. The invention of claim 1 wherein said coiled means for scattering ultrasonic energy comprises at least one member selected from the group consisting of copper, gold, silver, platinum, stainless steel, and alloys thereof.

11. The invention of claim 1 wherein said coiled means for scattering ultrasonic energy comprises a length in the range of approximately 3 to 7 millimeters.

12. The invention of claim 11 wherein said coiled means for scattering ultrasonic energy comprises a length of approximately 5 millimeters.

13. The invention of claim 1 wherein said ultrasonic transducer means comprises piezoelectric transducer means.

14. The invention of claim 1 wherein said ultrasonic transducer means comprises magnetostrictive transducer means.

15. A method of in vivo positioning of a catheter within a vascular system comprising the steps of:
    (a) providing an elongated balloon catheter, comprising a balloon, a proximal end and a distal end, with at least one coiled ultrasonic energy scattering device encapsulated by ultrasonically transparent material mounted thereon;
    (b) introducing the balloon catheter into the vascular system;
    (c) subjecting the balloon catheter to ultrasonic energy emitted from an ultrasonic transducer disposed externally of said vascular system; and
    (d) viewing ultrasonic energy scattered by the ultrasonic energy scattering device and thereby guiding the balloon catheter into the desired position in the vascular system.

16. The method of claim 15 wherein the step of providing a balloon catheter comprises the additional step f providing ultrasonic energy scattering devices at the proximal end and the distal end of the balloon catheter.

17. The method of claim 16 wherein the step of providing a balloon catheter comprises the additional step of providing ultrasonic energy scattering devices at the proximal end and the distal end internally of the balloon.

18. The method of claim 16 wherein the step of providing a balloon catheter comprises the additional step of providing ultrasonic energy scattering devices at the proximal end and the distal end externally of the balloon.

19. The method of claim 15 wherein the step of providing a catheter with an ultrasonic energy scattering device comprises the additional step of providing a plurality of discrete annular coils, wherein the distance between discrete annular coils is less than the length of the annulus diameter.

20. The method of claim 15 wherein the step of providing a catheter with an ultrasonic energy scattering device comprises the additional step of providing at least one helical coil.

21. The method of claim 15 wherein the step of subjecting the catheter to ultrasonic energy comprises utilizing a piezoelectric transducer.

22. The method of claim 15 wherein the step of subjecting the catheter to ultrasonic energy comprises utilizing a magnetostrictive transducer.

* * * * *